United States Patent [19]
Coppola

[11] Patent Number: 6,145,388
[45] Date of Patent: Nov. 14, 2000

[54] APPARATUS FOR SUPPORTING A FLUID SAMPLING DEVICE IN AN OPENING BELOW A MANHOLE COVER AND METHOD THEREFOR

[76] Inventor: Daniel D. Coppola, 4600 San Miguel, North Las Vegas, Nev. 89030

[21] Appl. No.: 09/133,096

[22] Filed: Aug. 12, 1998

[51] Int. Cl.[7] .................................................. G01N 1/00
[52] U.S. Cl. .................. 73/863; 73/864.91; 73/64.56; 356/244
[58] Field of Search ............................. 73/864.59, 864.84, 73/864.85, 864.91, 64.56; 248/85, 87, 205.1, 431; 356/244

[56] References Cited

U.S. PATENT DOCUMENTS 4,800,916  1/1989  Lakey ......................................... 248/87

*Primary Examiner*—Hezron Williams
*Assistant Examiner*—Thuy Vinh Tran
*Attorney, Agent, or Firm*—Harry M. Weiss; Jeffrey Weiss; Harry M. Weiss & Associates, P.C.

[57] ABSTRACT

An apparatus and method is disclosed for supporting a fluid sampling device in an opening below a manhole cover. The apparatus contains a triangular shaped assembly of three tubular members joined together at a common juncture. At least one of the tubular members has an extending member to adapt the triangular shaped assembly to be connected beneath a manhole cover of varying sizes for different sized openings in a street.

20 Claims, 1 Drawing Sheet

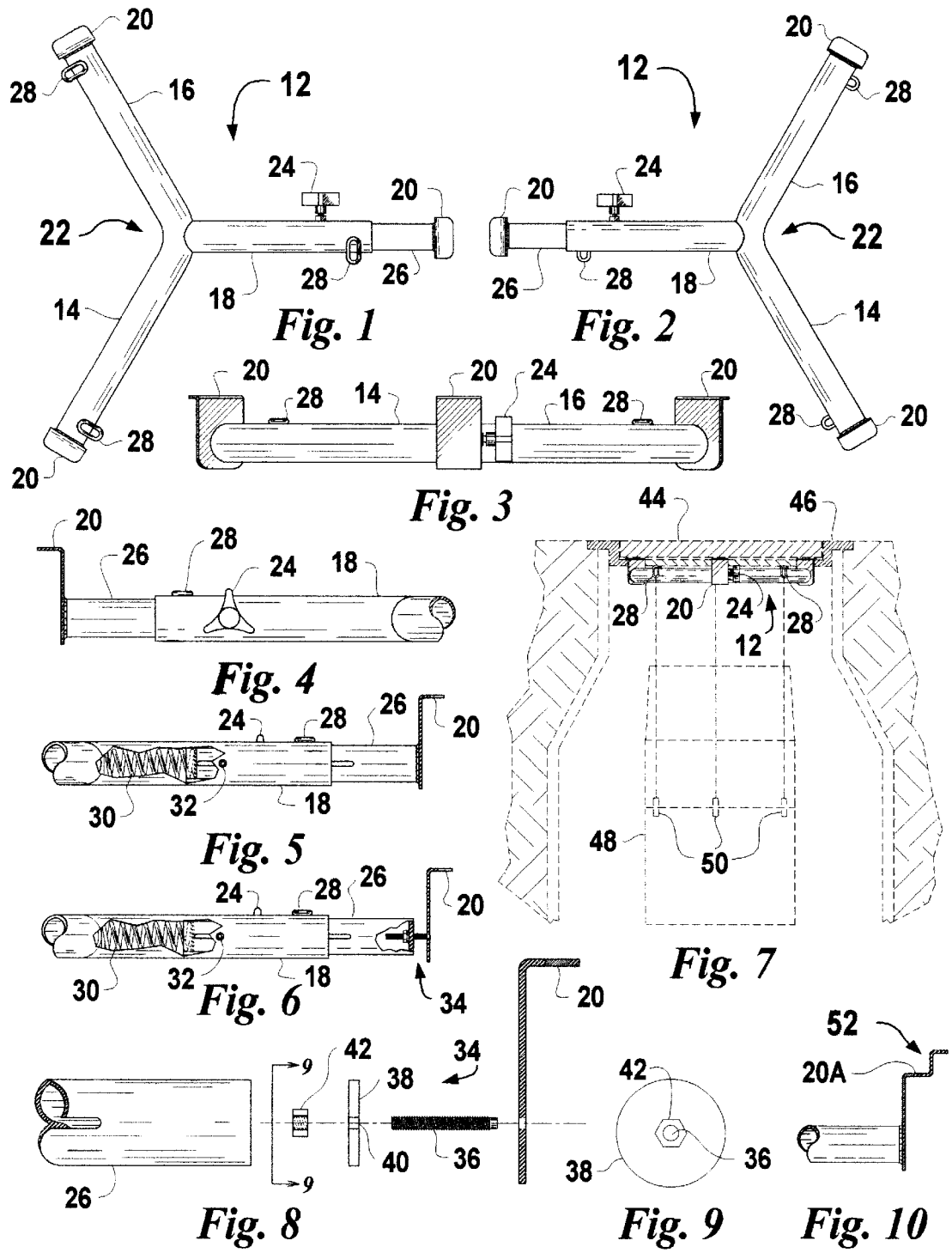

APPARATUS FOR SUPPORTING A FLUID SAMPLING DEVICE IN AN OPENING BELOW A MANHOLE COVER AND METHOD THEREFOR

FIELD OF THE INVENTION

This invention relates generally to underground sampling of fluids and methods therefor and, more particularly, to an apparatus for supporting a fluid sampling device in an opening below a manhole cover and a method therefor.

BACKGROUND OF THE PRIOR ART

Because of serious concerns relating to pollution and/or contamination of fluids that can eventually become part of the water supply of a community, it has become very important for the safety of the people in the community to be able to test flowing fluids including air to constantly check the contamination levels of the fluids.

Very often, industrial plants are located in or near a region that contains a lot of people who are dependent upon a supply of water from or near their region for drinking purposes. In some situations, the supply of water is from one or more wells that are used to extract water from a water table located beneath the surface of the land. In other situations, the supply of water is from a source of water such as a lake that is within or near the region of people.

For example, Lake Mead in Nevada is near the city of Las Vegas, Nev. and the water from Lake Mead is used as a primary source of water supply for the city of Las Vegas and surrounding areas. In this specific situation of Lake Mead, the water supply in this lake which is crucial for the people of the city of Las Vegas and surrounding areas is, unfortunately, the location where various effluent fluid discharges are directed due to the need to carry away these fluid discharges to be dumped into some large body of water.

Consequently, sewer lines from residential areas will carry effluent fluid discharges from residents to Lake Mead after passing through a treatment plant. Also, sewer lines passing through or near industrial plants or sites that discharge potentially toxic chemical fluids into their sewer lines can create a very serious water contamination problem to the water supply provided by Lake Mead. Therefore, these sewer lines passing through or near the industrial plants or sites need to be very carefully monitored in order to determine if effluent carried by these sewer lines are carrying toxic chemical fluids that can provide a serious source of contamination to the water supply of Lake Mead.

Various techniques have been developed to monitor the effluent fluids carried by the sewer lines passing in or through the industrial plants or sites. After various attempts using different techniques, it has been determined that an optimum effluent fluid testing or sampling procedure is to lower a fluid sampling device underneath a manhole cover of a sewer line in order to provide a way of obtaining fluid samples from the effluent stream.

Unfortunately, prior attempts at suspending a fluid sampling device underneath a manhole cover have not been very successful because of the instability of the apparatus used to suspend the fluid sampling device beneath the manhole cover. For safety reasons, the manhole cover needs to be kept on the hole or opening in the street where the manhole cover is located. Thus, vehicles such as cars, trucks, etc. whose wheels may go directly on the top surface of the manhole cover, can create impact forces on the manhole cover or create vibrations thereto which can cause fluid sampling attachment mechanisms located beneath the manhole cover to collapse thereby causing the loss of the attachment mechanisms and the fluid sampling devices connected thereto.

As a result, a need existed for an improved apparatus and method for supporting a fluid sampling device in an opening below a manhole cover which would be reliable, stable and have a positive force connection or attachment to withstand contact to or vibrations of the manhole cover and to also permit quick and easy adjustment to various size openings in the ground beneath the manhole cover and corresponding various sizes of the manhole cover.

SUMMARY OF THE INVENTION

Accordingly, it is an object of the invention to provide an improved apparatus and method for supporting a fluid sampling device in an opening below a manhole cover.

It is another object of this invention to provide an improved apparatus and method for supporting a fluid sampling device in an opening below a manhole cover which contains elements that provide a positive force connection or attachment between the perimeter of the opening and the manhole cover to thereby insure stability of the connection or attachment and prevent loss of the apparatus and the fluid sampling device attached thereto.

It is a still further object of this invention to provide an improved apparatus and method for supporting a fluid sampling device in an opening below a manhole cover which contains elements that both provide a positive force connection or attachment and permits adjustment or extension for use with varying sizes of manhole covers and openings therefor.

BRIEF DESCRIPTION OF THE PREFERRED EMBODIMENTS

In accordance with one embodiment of this invention, an apparatus is disclosed for supporting a fluid sampling device in an opening below a manhole cover which comprises, in combination: a triangular shaped assembly comprising three separate tubular shaped members each one of the three separate tubular shaped members joined at a common end portion with the other two of the three separate tubular shaped members; and means located at the other end portion of each of said three separate tubular shaped members for removably connecting each of said three separate tubular shaped members to an attachment position below the manhole cover. Preferably at least one of said three separate tubular shaped members having means for extending the other end portion in a linear direction in order to permit said triangular shaped assembly to be used with varying sizes of manhole covers covering various sized openings. In one example, the extending means having spring means for permitting said extending means to be extended in the linear direction when said spring means is expanded and for permitting the extending means to be retracted when said spring means is contracted. In one embodiment, extension means are located on an end portion of said extending means for further extending said extending means in the linear direction. The extension means comprises an apertured member having a rod shaped member extending therethrough, the rod shaped member having external threads, nut means threadably coupled to the rod shaped member for permitting the rod shaped member to move in a linear direction through the apertured member and for locking in a desired position the rod shaped member by contact with one side of the apertured member, and attachment means connected to one end portion of the rod shaped member for permitting one of said three separate tubular shaped members to be removably connected to the attachment position below the manhole cover. The triangular shaped assembly also comprises a plurality of ring means for permitting attachment of a corresponding plurality of wires thereto to support a fluid sampling device below the manhole cover.

In accordance with another embodiment of this invention, a method is disclosed for supporting a fluid sampling device in an opening below a manhole cover which comprises the steps of: providing a triangular shaped assembly comprising three separate tubular shaped members each one of the three separate tubular shaped members joined at a common end portion with the other two of the three separate tubular shaped members; and providing means located at the other end portion of each of the three separate tubular shaped members for removably connecting each of said three separate tubular shaped members to an attachment position below the manhole cover.

The foregoing and other objects, features and advantages of this invention will be apparent from the following more particular description of the preferred embodiments of the invention as illustrated in the accompanying drawings.

BRIEF DESCRIPTION OF THE FIGURES

FIG. 1 is a top elevational view of a triangular shaped assembly for use in an apparatus and method in accordance with this invention for supporting a fluid sampling device in an opening below a manhole cover.

FIG. 2 is a top elevational view similar to FIG. 1, but showing the triangular shaped assembly of FIG. 1 facing in the opposite direction from that shown in FIG. 1.

FIG. 3 is a side elevation and perspective view of the triangular shaped assembly of FIG. 1 when viewed from the right side of FIG. 1.

FIG. 4 is a side elevational view of a portion of one of the three tubular members of the triangular shaped assembly of FIGS. 1, 2 and 3.

FIG. 5 is an opposite side elevational view of the portion of one of the three tubular members of the triangular shaped assembly of FIG. 4 with a portion of the one tubular member broken away to show the spring inside thereof.

FIG. 6 is a side elevational view similar to FIG. 5, but depicting another embodiment where an extension means is used to extend the length of the one tubular member.

FIG. 7 is a side elevational view of the triangular shaped assembly of FIG. 1, 2 or 3 used below a manhole cover to permit a sampling device, connected to the triangular shaped assembly to be in position to sample effluent below the manhole cover.

FIG. 8 is an enlarged perspective and exploded view of the extension means shown in FIG. 6.

FIG. 9 is a front side elevational view of a portion of the extension means taken on the line 9—9 of FIG. 8.

FIG. 10 is a side elevational view of another embodiment of a flange member to be used with the extending member of FIG. 5 or the extension mechanism of FIGS. 6 and 7.

DESCRIPTION OF THE SPECIFICATION

Referring to FIGS. 1, 2, 3 and 4 reference number 12 generally refers to a triangular shaped assembly that is comprised of three tubular members 14, 16 and 18. The tubular members 14, 16 and 18 are preferably made of any suitable metal, however, if desired, plastic material or other materials may be used. Each of the tubular members 14, 16 and 18 (which are preferably 120 degrees apart from each other) have a flange member 20 at one end thereof and the three tubular members 14, 16 and 18 are joined together at a common juncture 22. The triangular assembly 12 also comprises a control knob 14 which functions to hold in place at any desired position extending member 26 that is used to extend the linear distance of the tubular member 18. The control knob 24 is turned such as in a clockwise direction to thereby insert a shaft coupled thereto into an opening in the tubular member 18 to provide pressure contact with the extending member 26 and thereby hold the extending member 26 in as a desired or selected position relative to the larger diameter of the tubular member 18. Thus, by telescoping the extending member within the tubular member 18 and using the control knob 24 a selected distance or length can be achieved for the tubular member 18 with its extending member 26. The operation and function of the flange members 20 for the tubular members 14, 16 and 18 is described below with respect to FIG. 7. Preferably, each of the tubular members 14, 16 and 18 has an elliptical shaped ring 28 attached thereto such as by welding. The purpose of these three elliptical shaped rings 28 is to permit a wire to be hung therefrom as shown in FIG. 7.

Referring to FIGS. 5 and 6, a spring 30 is shown as located within the tubular member 18 and the function of this spring is to apply an outward biasing force against an end portion of the extending member 26 so as to prevent the extending member 26 from being moved inwardly in the direction of the encircling tubular member 18. This also permits a better and more positive form of engagement for the triangular assembly 12 for the specific application shown in FIG. 7. If desired, air or hydraulic means can be used in place of the spring 30. A pin member 32 (see FIGS. 5 and 6) is used to penetrate through an opening (not shown) in the tubular member 18 to enter slot 34 within the extending member 26 to prevent an inadvertent or undesired twisting or rotation of the extending member 26 within the encircling tubular member 28 and also to prevent separation of these members.

Referring to FIGS. 6 and 8, an extension mechanism 34 is coupled to the end portion of the extending member 26 of the tubular member 28 to permit, in effect, an increased linear extension of the tubular member 18 and thereby permits the triangular assembly 12 to be adapted to be used with somewhat larger openings beneath a manhole cover. The extension member 34 is comprised of a threaded shaft 36 that is attached at one end to the flange member 20 such as by welding to an opening therein (see FIG. 8). The threaded shaft 36 is rotatably connected by means of its threads to disk 38 (that is fixed to the end of the extending member 26) by means of an aperture 40 located therein. Nut 42 serves to lock and position the threaded shaft 36 relative to the disk 38. Thus, the extension mechanism 34 can be extended or contracted as desired to extend or contract the flange 20.

Referring to FIG. 9, the assembly of the nut 42 on the threaded shaft 36 behind the disk 38 is shown for the fixed or locking position of the threaded shaft 36.

Referring to FIG. 7, the triangular assembly 12 is shown in position beneath a manhole cover 44 that is positioned within an opening in a street. The manhole cover 44 is placed within a suitable frame 46 that is located in the opening in the street. Thus, the flange member 20 at the end of each of the tubular arms 14, 16 and 18 of the triangular assembly 12 serves to attach or connect the tubular members 14, 16 and 18 and thus the triangular shaped assembly 12 to the frame 46 beneath the bottom perimeter edge portion of the manhole cover 44 due to the ninety degree bend in the flange member 20. Preferably, three wires extend downwardly from the three tubular members 14, 16 and 18 from the elliptical rings 28 thereof to support an instrument package 48 by means of clips or other desired forms of attachment devices 50 at the ends of the wires. The instrument package 48 is used to sample the effluent fluids below the manhole cover 44.

FIG. 10 depicts another variation of a flange member 20A that can be used instead of the flange member 20. The flange member 20A has an extra portion 52 that permits more positive attachment or connection because it can extend above the frame 46 and a small distance outwardly along the top surface thereof.

While the invention has been particularly shown and described with reference to the preferred embodiments thereof, it will be understood by those skilled in the art that the foregoing and other changes in form and details may be made therein without departing from the spirit and scope of the invention.

What is claimed is:

1. An apparatus for supporting a fluid sampling device in an opening below a manhole cover comprising in combination:
    a manhole cover;
        a triangular shaped assembly located adjacent to said manhole cover and comprising three separate tubular shaped members each one of the three separate tubular shaped members joined at a common end portion with the other two of the three separate tubular shaped members; and
        means located at the other end portion of each of said three separate tubular shaped members for removably connecting each of said three separate tubular shaped members to an attachment position below the manhole cover.

2. The apparatus of claim 1 wherein at least one of said three separate tubular shaped members having means for extending the other end portion in a linear direction in order to permit said triangular shaped assembly to be used with varying sizes of manhole covers covering various sized openings.

3. The apparatus of claim 2 including extension means located on an end portion of said extending means for further extending said extending means in the linear direction.

4. The apparatus of claim 2 wherein said extending means being located on only one of said three separate tubular shaped members.

5. The apparatus of claim 4 wherein said extending means having spring means for permitting said extending means to be extended in the linear direction when said spring means are expanded and for permitting the extending means to be retracted when said spring means is contracted.

6. The apparatus of claim 5 including extension means located on an end portion of said extending means for further extending said extending means in the linear direction.

7. The apparatus of claim 6 wherein said extension means comprising an apertured member having a rod shaped member extending therethrough, said rod shaped member having external threads, nut means threadably coupled to said rod shaped member for permitting said rod shaped member to move in a linear direction through said apertured member and for locking in a desired position said rod shaped member by contact with one side of said apertured member, and attachment means connected to one end portion of said rod shaped member for permitting said one of said three separate tubular shaped members to be removably connected to the attachment position below the manhole cover.

8. The apparatus of claim 7 wherein said triangular shaped assembly comprising a plurality of ring means for permitting attachment of a corresponding plurality of wires thereto to support a fluid sampling device below the manhole cover.

9. The apparatus of claim 4 wherein said extending means having spring means for permitting said extending means to be extended in the linear direction when said spring means are expanded and for permitting the extending means to be retracted when said spring means is contracted.

10. The apparatus of claim 9 including extension means located on an end portion of said extending means for further extending said extending means in the linear direction.

11. A method for supporting a fluid sampling device in an opening below a manhole cover comprising the steps of:
    providing a manhole cover;
    providing a triangular shaped assembly located adjacent to said manhole cover and comprising three separate tubular shaped members each one of the three separate tubular shaped members joined at a common end portion with the other two of the three separate tubular shaped members; and
    providing means located at the other end portion of each of said three separate tubular shaped members for removably connecting each of said three separate tubular shaped members to an attachment position below the manhole cover.

12. The method of claim 11 wherein at least one of said three separate tubular shaped members having means for extending the other end portion in a linear direction in order to permit said triangular shaped assembly to be used with varying sizes of manhole covers covering various sized openings.

13. The method of claim 12 including extension means located on an end portion of said extending means for further extending said extending means in the linear direction.

14. The method of claim 12 wherein said extending means being located on only one of said three separate tubular shaped members.

15. The method of claim 14 wherein said extending means having spring means for permitting said spring means are expanded and for permitting the extending means to be extended in the linear direction when said extending means to be retracted when said spring means is contracted.

16. The method of claim 15 including extension means located on an end portion of said extending means for further extending said extending means in the linear direction.

17. The method of claim 14 wherein said extending means having spring means for permitting said extending means to be extended in the linear direction when said spring means are expanded and for permitting the extending means to be retracted when said spring means is contracted.

18. The method of claim 17 including extension means located on an end portion of said extending means for further extending said extending means in the linear direction.

19. The method of claim 18 wherein said extension means comprising an apertured member having a rod shaped member extending therethrough, said rod shaped member having external threads, nut means threadably coupled to said rod shaped member for permitting said rod shaped member to move in a linear direction through said apertured member and for locking in a desired position said rod shaped member by contact with one side of said apertured member, and attachment means connected to one end portion of said rod shaped member for permitting said one of said three separate tubular shaped members to be removably connected to the attachment position below the manhole cover.

20. The method of claim 19 wherein said triangular shaped assembly comprising a plurality of ring means for permitting attachment of a corresponding plurality of wires thereto to support a fluid sampling device below the manhole cover.

* * * * *